United States Patent [19]
Lee et al.

[11] Patent Number: 5,250,023
[45] Date of Patent: Oct. 5, 1993

[54] TRANSDERMAL ADMINISTRATION METHOD OF PROTEIN OR PEPTIDE DRUG AND ITS ADMINISTRATION DEVICE THEREOF

[75] Inventors: Hai Bang Lee; Bung Chul Shin, both of Taejeon, Rep. of Korea

[73] Assignee: Korean Research Institute on Chemical Technology, Tae Jeon, Rep. of Korea

[21] Appl. No.: 604,498

[22] Filed: Oct. 29, 1990

[30] Foreign Application Priority Data

Oct. 27, 1989 [KR] Rep. of Korea .................. 89-15519
May 22, 1990 [KR] Rep. of Korea .................... 90-7357

[51] Int. Cl.$^5$ ............................................. A61N 1/30
[52] U.S. Cl. ............................ 604/20; 128/898; 607/153
[58] Field of Search ........................ 604/20, 46, 49; 128/743, 798, 898, 802, 803; 606/131

[56] References Cited

U.S. PATENT DOCUMENTS

| | | | |
|---|---|---|---|
| 3,136,314 | 6/1964 | Kravitz | 604/46 |
| 4,473,083 | 9/1984 | Maganias | 604/46 |
| 4,722,726 | 2/1988 | Sanderson et al. | 604/20 |
| 4,842,577 | 6/1989 | Konno et al. | 604/20 |
| 4,878,892 | 11/1989 | Sibalis et al. | 604/20 |
| 4,927,408 | 5/1990 | Haak et al. | 604/20 |
| 4,940,456 | 7/1990 | Sibalis et al. | 604/20 |
| 5,003,987 | 4/1991 | Grinwald | 604/20 |
| 5,084,006 | 1/1992 | Lew et al. | 604/20 |

*Primary Examiner*—Stephen C. Pellegrino
*Assistant Examiner*—Midrad Rafa
*Attorney, Agent, or Firm*—Cushman Darby & Cushman

[57] ABSTRACT

A transdermal administration method for protein or peptide drug that contacting and ionizing a protein or peptide drug immersed in hydrophilic polymer with ionizing solvent composition, and forming the drug pathway on epidermis by plural skin needles or treating the skin by a razor, and transferring the above ionized drug into the skin by electric force.

19 Claims, 3 Drawing Sheets

TRANSDERMAL ADMINISTRATION METHOD OF PROTEIN OR PEPTIDE DRUG AND ITS ADMINISTRATION DEVICE THEREOF

Figure 1:
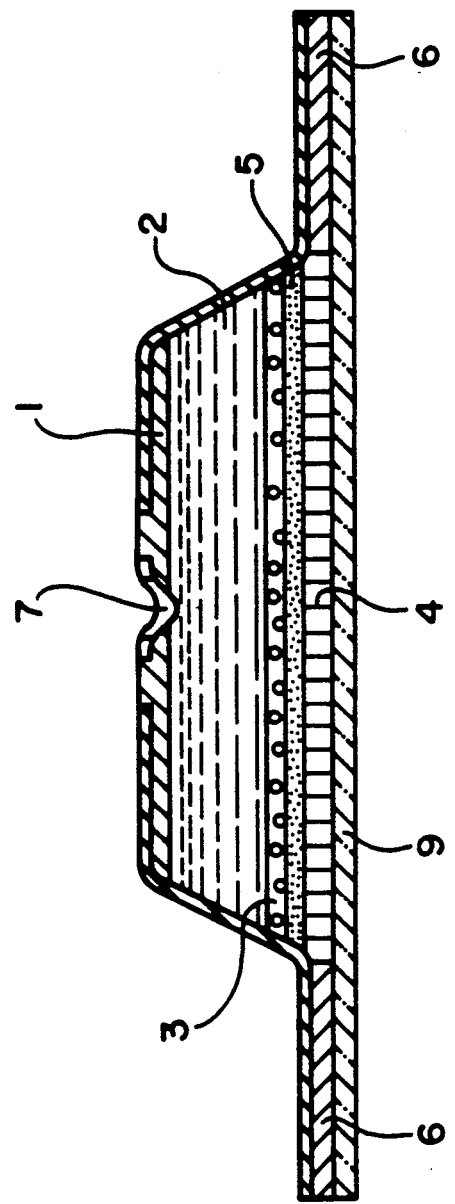
FIG. 1 is a vertical section of an integration-type transdermal administration device as one embodiment according to this invention.

| 1.11 | Electrode | 2.12 | Solvent reservoir |
|---|---|---|---|
| 3.13 | Drug reservoir | 4.14 | Skin stimulate needle |
| 5 | Skin stimulate needle supporter | 6.16 | Adhesive layer |
| 7 | Solvent inlet | 15 | Skin stimulate needle plate |
| 18 | Semipermeable membrane | 9.19 | Released paper |
| 30 | Patch body | | |

DETAILED EXPLANATION OF THIS INVENTION

The invention relates to the transdermal administration method of a protein or peptide drug and its administration device thereof and more particularly, to the method of transdermally administering the ionized drug by electric force after dissolving and ionizing a protein or peptide drug with an ionizing solvent, also to the transdermal administration device designed for applying such method efficiently and conveniently.

Generally, in delivering of a protein or peptide drug (i.e., insulin as physiological metabolism modulator, interferon as anticancer agent, and captopril as cardiovascular modulator) into the human body, some administration methods such as oral administration, injectables, mucosa delivery agent and pump transplant have been commonly used, but such methods caused some side effects and their use was inconvenient, let alone the psychological discomfort to patients.

To comply with this matter, some researchers have recently studied the transdermal administration method of delivering a protein or peptide drug into skin. Among other things, a most attractive method is transferring a protein or peptide drug having electric charge into the epidermis by an electric current.

For instance, R. L. Stephen et al, Biomed, Biochem. Acta 43(1984)5, 553–558, tried to deliver insulin into a pig's skin through the transmission of constant electric current but the result was unsuccess due to the insufficient electric charges of insulins and to the failure of making its monomer.

Thereafter, another method to deliver the insulins into the human body by removing the stratum corneum was made but, this method has been associated with some problems including infections incurred out of removing epidermis and the undesirable transformation/treatment of the skin. Also, the method of delivering insulin without any skin bruise was studied again by using pulse current. However, this proved to be inefficient because of the insufficient dose of the drug delivered and short duration of drug effect in the body.

In the meanwhile, R. R. Bilrnette and D. Marerro. J. Pharm. sci., 75:738(1986) experimented to transdermally administer TRH (Thyrotropin releasing hormone), a hormone of extending by iontophoresis the pregnancy and lactation of women. Further, J. E. Marchand and N. Hagino, J. Urol., 97:874(1982) exemplified in animal experiment the possibility of administering Vasopressins into the skin.

Also, B. Robent Meyer et al. clin. pharm & Therape, 44, 6, 607 (1988) tried to deliver LH (Luteinizing Hormone) across the skin by a direct current.

However, the aforementioned methods have recognized several disadvantages as follows: When a protein or peptide drug is delivered transdermally, its molecular chains are susceptible to being destroyed by electric current and the depression of biological activities occurred. Moreover, since the delivery of required amount is not available once a time because of the high permeation resistance in skin, only a small percentage of the drugs should be transdermally delivered in several divided times. Besides, the transdermal delivery might raise other specific problems such as skin irritation/impairment and more potent use of enhancer might also induce the deformation of human skin system.

Therefore, one of the objects of the present invention is to provide an efficient method, wherein by skin stimulate needle(hereinafter "skin needle"), a sufficient amount of protein or peptide drug can be transdermally delivered into the skin on a continual basis with reduced side effects.

It is another object of the present invention to provide a transdermal administration device comprising the storage reservoir of ionizing solvent, drug reservoir and skin needle, through which the sustained administration of a protein or peptide drug may be available for three to four days by a simple one-time treatment.

It is a further object of the present invention to provide the composition of ionizing solvent which function is: Dissolving a protein or peptide drug having more than three peptide units of amino acid into the monomer, and increasing an ionization degree, and enabling the said drug to efficiently pass through the epidermis layer.

The detailed description of this invention is as set forth hereunder:

The invention relates to the transdermal administration method of a protein or peptide drug being characterized by the following procedure: Contacting and ionizing a Protein or peptide drug immersed in polyelectrolyte with the composition of ionizing solvent consisting of solvent, polyelectrolyte arid enhancer, and forming the drug delivery pathway into the skin by a electric razor, and penetrating the above ionized drug into the skin by electric force.

One embodiment of the transdermal administration device according to this invention is an integration-type transdermal administration device as patch-type used by attaching to the skin, in which:

A) reservoir(2) of ionizing solvent on the upper side forming an electrode(1) being open to the outside B) drug-immersed hydrophilic polymer drug reservoir(3) forming the lower part C) water-swelling polymer skin needle supporter(5) where plural skin needles(4) are vertically dispersed in a fixed state D) stacking-structure adhesive layer(6) formed around the said skin needle supporter(3) F) Solvent inlet(7) placed in the upper central part of the said storage reservoir(2).

Another embodiment of the transdermal administration device according to this invention is a separation-type transdermal administration device as patch-type used by attaching to the skin, in which:

A) Reservoir(12) of ionizing solvent on the upperside forming an electrode (11) being open to the outside B) semipermeable membrane (18) with a molecular cut-off ranging from 200 to 20,000 while forming the lower side of the reservoir(12) C) drug-immersed hydrophilic polymer drug reservoir(13) D) patch body(30) composed of adhesive layer formed around the said drug supporter(13) E) skin needle plate(15) in which skin needles(14) on water-swelling polymer sheet are vertically distributed in a fixed state.

Also, this invention relates to the composition of ionizing solvent, in line with the solvent dissolving and ionizing a protein or peptide drugs, which consists of: In proportion to water 100% by volume, 1 to 50% by volume of any one or more mixture solutions selected from sodium acetate, sodium-EDTA, sodium salicylate, salt buffer solution of phenol derivatives, acetic acid, hydrochloric acid, ammonia water, and caustic soda; 1 to 30% by volume of polyelectrolyte; 1 to 30% by volume of enhancer.

This invention can be described in more detail as set forth hereunder: In general, a protein or peptide drug being used in the treatment of various human diseases has its innate isoelectric point wherein its dissolution is made available only in case of exceeding the isoelectric point or in a lower pH. Since such drug has a constant dipole polarity, the ionization of monomeric drug having the positive or negative electric charge depends on the pH of solvent.

Therefore, in case a target drug having cation (less than the isoelectric point of the drug), anode is used and cathode used in anionic drug (more than the isoelectric point). Thus, a drug may be transferrable by an electric repulsion force.

By applying such principle, this invention relates to the method of administering a protein or peptide drug across human skin; in this invention, the ionizing solvent used in dissolving a protein or peptide drug into monomer having either cation or anion, uses the composition of ionizing solvent comprising the following: In proportion to water 100% by volume, 1 to 50% by volume of solvent, 1 to 30% by volume of polyelectrolyte, and 1 to 30% by volume of enhancer.

Here, the solvent of main ingredient may be used by selecting some, organic/inorganic acids and organic/inorganic bases such as sodium acetate, sodium-EDTA, sodium salicylate, and salt buffer solution of phenol derivatives, acetic acid, hydrochloric acid. ammonia water, and caustic soda. However, in case of using cathode, the solvent such as inorganic or organic base or salt buffer solution should be used and in case of using anode, the solvent such as inorganic or organic acid be used.

If the electrode of polyelectrolyte which plays a role to prevent the pH change of solvent by electrolyis is anode, any one or more soluable(or insoluable) polymers may be used in the following: polyacrylamide(-more than M.W. 10,000), polyvinylamine(more than M.W. 10,000), quadrivalent ammonium, or pyridinium. If the electrode is cathode, any one or more solvents may be used as the ph-controlling polyelectrolyte in the following: polyacrylic acid, carboxymethylcellulose (C.M.C), alginic acid. When the above polyelectrolyte is added, the pH change of electrode is described in Table 1.

TABLE 1

| pH Resistance of 1% polyelectrolyte solution after applying 1 mA current for 2 hrs. | | |
|---|---|---|
| Polyelectrolyte | pH Change of Cathode | pH Change of Anode |
| Polyacrylamide | — | 7.5 → 9.1 |
| Polyvinylamine | — | 7.5 → 7.9 |
| Polyacrylic acid | 7.0 → 6.6 | — |
| C.M.C. | 7.0 → 4.3 | — |
| Alginic acid | 7.0 → 4.4 | — |
| D.I. Water | 7.0 → 1.8 | 7.5 → 12.5 ./5 |

In order to facilitate the drug delivery, any one or more enhancers is/are used by selecting the following:
(a) EDTA as chelating agent, citric acid, N-alkyl derivative
(b) bile salts(sodium dioxychelate, sodium tarocholate)
(c) fatty acids(oleic acid mono-olein, saponin)

Meantime, in this invention, the electric current having a density ranging from 0.01 to 1 mA/cm should be used. And a pulsating current in its type is more preferable than a direct current because the occurence of impedance by the current leads to the great increase of resistance and voltage, thus being vulnerable to skin burn, while the pulsate current source to eliminate the impedance wherein high currents may be available under the low voltage.

By way of example to make the operation of the invention more clear, reference is made to the accompanying drawings.

FIG. 1 is an integration-type transdermal administration device embodying the concept of the present invention in which: Solvent reservoir(2) made of plastic film (e.g. polyethylene or polyethylene terphthalate). supporting the frame of device itself and having no solvent permeability and on the upper side, electrode (1) and solvent inlet(7) are open to the outside. The said electrode(1) consists of metal sheet comprising silver, lead or tin and the solvent inlet is made of "V" type rubber, so that under the air-tight condition from the outside, the composition of ionizing solvent may be injected into solvent storage reservoir(2) by a syringe.

In the lower part of the said solvent reservoir(2), drug reservoir (3) comprising drug-immersed(in powder) hydrophilic polymer layer is formed. The soluble polymers usable as the said drug reservoir(3) are polyacrylamide, carboxymethylcellulose, polyvinylimine, polyacrylate, alginate, karaya gum, and gelatin. The major functions of the water soluble polymer are to support the drug, heighten the drug permeability by hydrating the human skin.

In the skin needle supporter(5) stacked at the lower part of the said drug supporter(3), 1 to 15 pieces of skin needle(4) per the unit area ( cm ) is/are dispersed in a fixed state, of which length protruding to the outside of drug supporter should be 0.2 to 2 mm. The skin needle(4) according to this invention has the diameter ranging from 50 to 400 μm, of which quality may be a steriled stainless steel.

If the diameter of skin needle(4) exceeds 400 μm, it is very difficult to permeate the skin and if smaller, the manufacture of skin needle is not easy. However, it appears that the thickness of skin needle(4) does not greatly affect the permeable amount of drug. Also, the protruding skin needle(4) in more than 2 mm long leads to the bruise of the capillary vessel in corium layer, thus causing a coagulation. If the length of skin needle is less than 0.2 mm, the needle cannot permeate the skin, thus resulting in a drastic decrease in deliverying the amount of drug.

Should the distribution of skin needle(4) per unit area of skin needle supporter(5) be overly high, a excess of drug might be delivered and the skin's injection might not be neglected after treatment. However, if small, the drug delivery effect of sustantial amount cannot be expected. The skin needle supporter(5) is made of water-swelling polymers and some of available polymer is the same as the case of drug reservoir(3).

The said skin needle supporter(5) is surrounded by the adhesive layer (6) which allows the attachment of a administration device to skin, and these skin needle supporter(5) and adhesive layer(6) are covered with released paper(9).

The use of an integration-type transdermal administration device is as follows: Injecting the ionizing solvent into solvent reservoir (2) through solvent inlet(7) by a syringe and so on, and removing released paper from the device, and compressing the device to the skin using adhesive layer(6). Then, connecting any one of anode or cathode to the electrode protruding on the upper side according to the kinds of drug or solvent, and having the opposite electrode connected to a conductive pad, e.g. karaya gum, etc. (not illustrated), then, attached to the side of the device, or connected to other device, then, usable two devices simultaneously.

In this way, the composition of ionizing solvent stored in solvent reservoir(2) dissolve the drug contained in drug reservoir(3), and ionizes the drug into cation or anion: the ionized drug moves to the, skin by the electric force with the electrode(1). Meantime, the skin needle(4) attached to skin needle supporter(5) may penetrate the epidermis layer by compression power, when the administration device is attached to the skin, thus forming the pathway for the drug delivery. With the lapse of time, when a solvent permeates from solvent reservoir(2). the skin needle supporter(5) become swelled by water swelling effect and the skin needle comes out from the skin.

However, if no electric current is applied to the pathway formed by skin needle(4), drugs claimed in this invention cannot penetrate across the skin mainly because the hydrophobic epidermis layer does not allow the permeation of hydrophilic drug and the passway formed by skin needle(4) is temporary closed by the swelling of skin.

Therefore, the electric current applied in the device makes the ionized drug and solvent move toward the opposite electrode, and then, the hydrophilic protein and polypeptide of the skin become arranged in equilibrium toward cathode, which cause a "contraction" of the skin. By the above phenomenon, the pathway of epidermis layer becomes open and the drug in the pathway may penetrate into corium layer.

Figure 2:
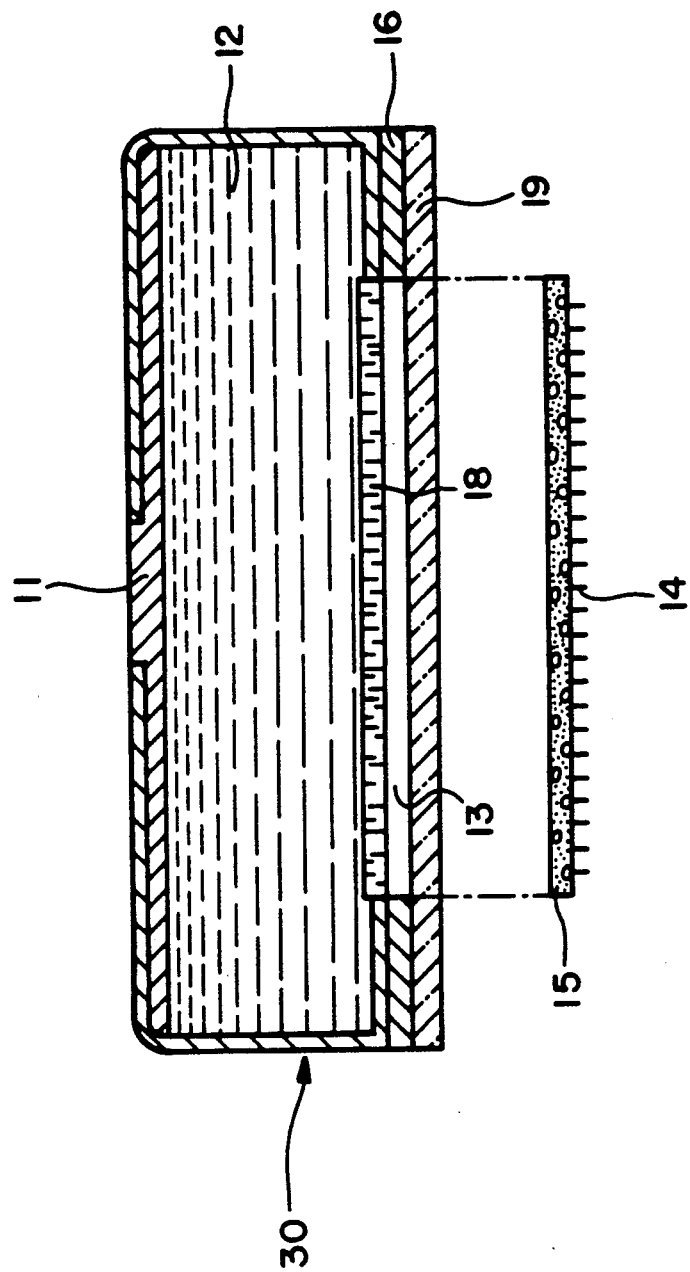
FIG. 2 is a vertical section of a separation-type transdermal administration device as another embodiment according to this invention.
Figure 3:
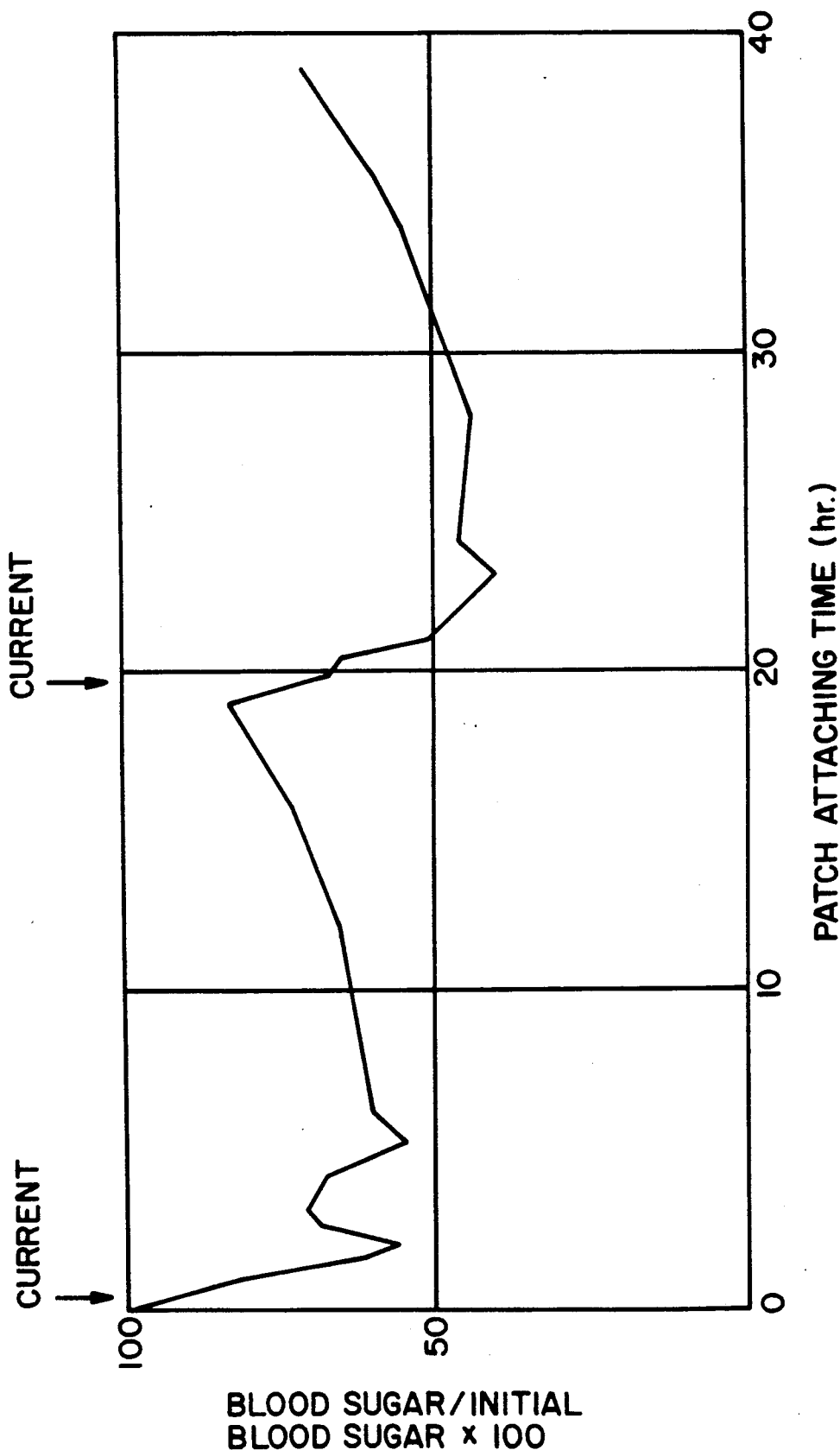
FIG. 3 is a graph showing the change of blood glucose level with the lapse of time when insulin is administered transdermally in accordance with EXAMPLE 4 of this invention.

Meantime, FIG. 2 as enclosed herein is a separation-type transdermal administration device embodying another concept of the present invention in which a patch body and skin needle plate(15) are separated.

The said patch body is made of the following: A) solvent reservoir (12) where ionization solvent is stored B) semipermeable membrane consisting of the lower part C) drug reservoir(13) where the drug is dispersed D) adhesive layer(16) E) released paper(19); In addition to that, there are several skin needles(14) are fixed vertically in the skin needle plate separated from the body frame.

The characteristics of a separation-type device are that since the ionizing solvent is already contained in the device, the administration of another ionizing solvent is unnecessary; there 13 a semipermeable membrane(18) between ionization solvent reservoir(12) and drug reservoir (13); there is a skin needle plate separated from the patch body.

The semipermeable membrane(18) whose molecular cut-off is in the level ranging from 200 to 20,000 is rather preferable, because the selection of semipermeable membrane(18) having less molecular cut-off than that of delivery drug prevents tile reduction of drug activity as the drug is not mixed in solvent reservoir-(12).

The semipermeable membrane to be used in this invention is selected from the following: polypropylene, cellulose, and ethylene vinylacetate. By making the molecular cut-oft of semipermeable membrane smaller than that of drug and polyelectrolyte contained in ionizing solvent, the latter cannot permeate the membrane. Then, the pH of ionizing solvent, remains unchanged and the skin irritation can be eliminated by preventing the contacts between polyelectrolyte and skin. Thus, the solvent molecule and enhancer only can pass through the semipermeable membrane(18).

The formation of skin needle plate(15) should be the same as that of skin needle placed in an integration-type administration device and the common type of textile fiber is rather advisable.

The method of using a separation-type administration device is as follows: Lightly compressing a skin needle plate(15) on the skin, and forming the drug delivery pathway on skin, and removing the skin needle plate(15), and on that skin, compressing the patch body(30) removing a released paper(19). The operation and principle of other parts are the same as those of an integration-type device.

However, the method of using a separation-type administration device is as follows: Lightly shaving the skin by a common type of razor without using the skin needle plate(15), and alleviating the permeation resistance of epidermis layer, and on that skin, compressing the patch body(30) removing a released paper(19).

Meantime, a protein or peptide drug applicable to this invention includes the following: as t-.he drugs having more than three peptide bond units in amino acid, for example, cardiovascular modulator (captopril, bradykinin, atriopeptin, calcitonin gene tactor, C.N.S. cholecystokinin(CCK-8, 32) as C.N.S. active peptide, $\beta$-endorphin, nerve growth factor, melanocyte inhibitor-I, gastric modulator (gastrin antagonis, neuro-tension, somatostatin), antibiotics & anticancer drugs(interferon, cyclosporin, encephalins), and biological metabolism modulator(albumin, insulin, vasopressins, oxytocin, growth hormone, LH(Luetinizing Hormone), TRH(Thyrotropin Releasing Hormone).

Referring to the influx mass of a protein or peptide drug in this invention, the ionophoresis of the ionized drug can be described as follows:

$$J = -D\frac{de}{dx} + \frac{D_2 \cdot Z \cdot e \cdot E \cdot C}{KT}$$

Where M is the mass of the drug delivered, D is the diffusion coefficient of nonionized class. D is the diffusion coefficient of ionized class, Z is the number of electric charge in molecular, e is an ionized degree, E is a potential difference, C is the concentration of ionized class, K is a Planck's constant, T is an absolute temperature.

As shown in the above formula, a higher electric (conductivity of solution makes the ionized classes dominate the diffusion in a more competitive manner. As a result, the diffusion of nonionized class can be neglected because of "dc/dx=0".

Thus, the above formula is expressed as follows:

$$J = \frac{D_2 \cdot Z \cdot e \cdot E \cdot C}{KT}$$

In general, there is a method of increasing the number of electric charge(Z) to heighten the electric current of ionized drug: in case the drug having limited number of electric charge is bound with the function group such as sulfate base having plentiful numbers of electric charge, the drug derivatives of increased numbers of electric charge may be obtained. Such drug derivatives may be more ionized than the general drugs which has relatively less number of electric charge among solvents and further, their competitive movement by being highly sensitive to the electric current results in increasing the mass of the drug delivered.

With reference to the ionized degree "e" as described in tile foregoing, of its ionization rate will increase in accordance with the selection of ionizing solvent. Therefore, as the ionization solvent, organic/inorganic acid and organic/inorganic salt base may be used; as the case may be, it may be used as the type of salt such as sodium chloride, phosphate or organic acid salts.

The invention will now be illustrated by the following examples.

EXAMPLE I

Manufacture of Integration-type Administration Device

Adding an aqueous solution of 0.5M sodim salicylate containing 1% polyacrylic acid salts(brandname: Carbopol) into 100 IU/ml insulin, and dispersing this mixture evenly. Then, adding 3 mg/ml phenol and 16 mg/ml glycerin into this mixture and mixing them sufficiently at less than 10° C., and thus, manufacturing the gel mixture of drug supporter.

On a sheet woven by polypropylene fibre, meantime, fixing 100 μm of T-type skin needle in diameter in a range of 10 pieces/cm toward the bottom from the upside, and paving the opposite sheet phase of protruding skin needle with the gel mixture of said drug reservoir evenly, and drying it by a freezing dryer, and thus, manufacturing both drug reservoir and skin needle supporter.

In a following manner, heat-sealing the said drug supporter and skin needle supporter to the lower side of already manufactured solvent storage reservoir by polyethylene terephthalate, and applying an adhesive layer and released paper to the fringe, and thus, manufacturing an integration-type administration device.

Meantime, the composition of ionizing solvent usable in the said integration-type administration device should contain 0.5M sodium salicylate salt butter solution containing 3% polyacrylamide, 3 mg/ml phenol, 16 mg/ml glycerin, and 1% saponin. Such ionizing solvent is added into the solvent storage tank prior to using the said integration-type device.

EXAMPLE 2

Manufacture of Separation-type Administration Device(1)

Adding the composition of ionizing solvent into polyethylene solvent reservoir attached with silver electrode, and heat-sealing in a row the cellulose membrane having a molecular cut-off of 3500 and already manufactured drug reservoir placed in the lower side. The composition of ionizing should contain citric acid at pH 3, 0.2% polyacryl acid(M.W. 150,000), 3.5 mg/ml phenol, 16 mg/ml glycerin, and a small amount of polyoxyethylene ethet.

The manufacture of drug supporter is as follows: Completely dissolving 100 IU/ml insulin and citric acid at pH 3 to porous polyurethanefoam, mixing it with 10% polyacrylate salts(brandname: Carbopol), and drying in a vacuum.

On a flexible aluminium foil, meantime, fix vertically T-shape skin needle in a range of 10 pieces/cm, and on the top of that, paving a sheet woven by polyestere, and by completely fixing the said needle with adhesives, and thus, manufacturing the skin needle plate. The manufacture of other parts is the same as that of Example 1.

EXAMPLE 3

Manufacture of Separation-type Administration Device

The composition of ionizing solvent compositions should contain 1M sodium acetate, 0.1% polyethyleneimine (M.W. 200,000), 3 mg/ml phenol, 16 mg/ml glycerin, and a small amount of mono-olein.

Semipermeable membrane should use the cellulose membrane having the molecular cut-off of 1,000. The manufacture of drug supporter is as follows: Adding 35% alginate gel containing 1M sodium acetate into 100 IU/ml and a small amount of phenol & glycerin, and mixing this mixture sufficiently, and drying it by freezing.

EXAMPLE 4

Use of Integration-type Administration Device

Shaving around the back hair of a white New Zealand-origin rabbit, and measuring its blood glucose, and attaching it to an integration-type administration device as manufactured in accordance with Example 1. Then, attaching cathode to the electrode, and having anode of the opposite connected to E.C.C electrode (brandname: Biolect) made from karaya gum, and transmitting the electricity of 0.5 mA, 2 KHz for 20 mins.

As a result of conducting the said procedure concerning 20 experiment animals, it was noted that the average blood glucose level was decreased from 100 mg/dl to 60 mg/dl within 6 hours. And such effect was maintained for 12 hours. The No. 4 table as enclosed herein illustrated the result of this Example.

EXAMPLE 5

Use of Separation-type Administration Device

Shaving around the back hair of a white New Zealand-origin rabbit, and lightly compressing a skin needle plate of a separation-type administration device as manufactured in accordance with the said Example 2, and removing the plate, and on the top of that, attaching a patch body.

Then, attaching cathode to the electrode, and having anode of the opposite connected to E.C.C. electrode, and transmitting the electricity of 0.5 MA, 2 KHz for 20 mins.

As a result of measuring the average blood glucose level concerning 20 experiment animals, it was decreased from 100 mg/dl to 50 mg/dl within 4 hours. And such effect was maintained for 12 hours.

Example 6

Simultaneous Use of Both Integration- and Separation-type Administration Devices By attaching cathode to an integration-type administration device of EXAMPLE 1 and having anode of the opposite connected to a separation-type administration device, the experiment was conducted in a same way as did in both Example 4 and 5.

As a result of measuring the average blood glucose level concerning 20 experiment animals, the said level was decreased from 100 mg/dl to 30 mg/dl within 4 hours. 17 animals among them were dead due to hypoglycemia within 8 hours.

EXAMPLE 7

Use of Electric Razor

This Example was conducted in a same way as did in Example 5 using a seperation-type administration device in Example 2: Shaving the back hair of a rabbit by a electric razor instead of the skin needle plate, and attaching it to a patch body of a separation-type administration device.

As a result of measuring the average blood glucose level concerning 20 experiment animals, it was decreased from 100 mg/dl to 50 mg/dl within 4 hours. 15 animals among them showed less than 20 mg/dl hypoglycemia within 12 hours.

EXAMPLE 8-11

This Example was conducted in vitro with a separation-type administration device in Example 2 by changing any administered drugs into insulin( Example 8), T.R.H( Example 9), L.H.( Example 10), and cacitonin( Example 11) respectively.

Fixing the outer surface of mouse skin to the adhesive part of administration device, arid fixing the diffusion cell adding saline solution in the inside, and treating it by the electric current of 0.1 mA for 20 mins, while connecting an administration device and diffusion gel to the electrode.

The drug in a diffusion cell delivered through the mouse skin was separated and assayed by HPLC and the result was described in Table 2.

TABLE 2

Drug delivery in diffusion cell through the mouse skin

| Hour | EXAM. 8 (Insulin/IU) | EXAM. 9 (TRH/mM) | EXAM. 10 (LH/mM) | EXAM. 11 (Calcitonin/ IU) |
|---|---|---|---|---|
| 2 | 3.0 | 22 | 8 | 4 |
| 4 | 4.4 | 31 | 12 | 10.5 |
| 8 | 9.8 | 45 | 15 | 15.1 |
| 12 | 12.4 | 70 | 16 | 26.7 |
| 18 | 14.7 | 83 | 21 | 32.1 |

A transdermal administration method for protein or peptide drug according to this invention has the following merits: a) may prevent the transformation of drug, by separating the ionizing solvent from the drug and avoiding a contact between the drug and electrode b) may prevent the reduction of drug's activity owing to the pH change of solvent by using a pH-controlling polyelectrolyte.

Further, since a drug is immersed in water-soluble polymer, the skin-administration effect of drug can be enhanced by contacting a high-concentrated drug with the skin and hydrophilizing the skin. Furthermore, the use of a skin needle and/or razor makes it possible to form the drug delivery pathway on epidermis, thereby solving the following specific problems as shown in the transdermal administration of protein or peptide drug, i.e. insufficiency of drug delivered, the transformation of skin owing to chemical enhancer or electric irritation, and the reduction of drug's activity in the skin. Along these lines, the sustained transdermal administration of the said drug may be available for three to four days by one-time use.

Meantime, the comparison between the skin treatment of razor and drug administration of skin needle according to this invention is shown below.

Data on the delivery effect of insulin based upon the skin treatment by using a skin needle and razor

| Hour | Control (No insulin) | Blood Glucose Level of Rabbit (mg/dl) | |
|---|---|---|---|
| | | Skin Needle | Razor |
| 0 | 115 | 104 | 104 |
| 2 | 115 | 54 | 64 |
| 4 | 110 | 66 | 53 |
| 6 | 99 | 52 | 47 |
| 8 | 103 | 60 | 40 |
| 10 | 102 | 65 | 11 |

Remarks:
a) Condition of electric current: 0.5 mA, on/off = 1
b) Treatment time: 20 mins
c) Skin needle: 3 pieces/cm
d) Razor: Treated by an electric razor for 20 secs The change of blood glucose in rabbit by the treatment of electric razor

| Hour | Blood Glucose Level of Rabbit (mg/dl) | | | | |
|---|---|---|---|---|---|
| | 2 secs. | 10 secs. | 20 secs. | 40 secs. | 60 secs. |
| 0 | 107 | 125 | 104 | 119 | 101 |
| 2 | 88 | 105 | 64 | 70 | 86 |
| 4 | 100 | 91 | 53 | 55 | 71 |
| 6 | 92 | 86 | 47 | 17 | 41 |
| 8 | 87 | 88 | 40 | low | 24 |
| 10 | 113 | 72 | 11 | dead | dead |

The delivery effect by the razor has not been fully established in its mechanism. We assume that like that of skin needle, the mechanism by the razor might be as follows: Reducing the resistance of drug's permeability into the skin, faciltating the electric current and thus, easily permeating the drug into the skin.

The thickness of epidermis is, even if variable, said to be in the range of 0.2 to 0.01 mm. By treating the epidermis by a razor, the upper part is partially removed and results in increasing the permeability of drug and electric conductance. In other words, similer case can be seen that an alcoholic lotion treatment after shaving gives a feeble irritation.

In case of a skin needle, although there is little skin resistance in the permeation pathway across the skin, the whole delivery effect is negligible small because of a limitation of usable skin needles. The blood glucose level of rabbit treated by an electric razor is lower than that of skin needle, which may be due to the tact that electric razor, gives large surface area of treated skin compared to that of skin needles.

What is claimed is:

1. An integration-type transdermal administration device of a patch-type which may be attached to the skin comprising the following:
   A) solvent reservoir (2) for ionizing solvent and polyelectrolyte, injected from the outside through a solvent inlet (7),
   B) drug reservoir (3) comprising drug immersed water-swellable polymer located opposite from the solvent inlet such that the solvent reservoir (2) is interposed between the drug reservoir and the inlet, with a lower portion support (5) made of non-woven fabric, including plural skin needles (4) vertically dispersed in a fixed state on said support and said support (5) is interposed between the drug reservoir and the skin needles,
   C) stacking-structural adhesive layer(6) formed around the supporter of the drug reservoir.

2. The integration-type transdermal administration device according to claim 1, wherein the solvent reservoir (2) and drug reservoir(3) are, constructed from one or more of the polymers from the group consisting of polyacrylamide, carboxymethylcellulose, polyvinylimine, polyacrylate, alginate, karaya gum, and gelatin.

3. The device according to claim 1 wherein the drug reservoir contains a drug selected from the group consisting of captopril, bradykinin, atriopeptin, calcitonin-gene factor, cholecystokinin (CCK-8, 32), β-endorphin, nerve growth factor, melanocyte inhibitor -I, gastrin antagonist, neuro-tension, somatotatin, interferon, cyclosporin, encephalins, albumin, insulin, vasopressins, oxytocin, growth hormone, LH (Leutinizing Hormone) and TRH (Thyrotropin Releasing Hormone).

4. The device according to claim 1 wherein the ionizing solvent in the solvent reservoir contains 1 to 50% by volume of solvents selected from the group consisting of salt buffer solutions of phenol derivatives, acetic acid, hydrochloric acid, ammonia water, and caustic soda.

5. The device according to claim 1 wherein the polyelectrolyte contained in the solvent reservoir contains 1 to 30% by volume of one or more polyelectrolytes selected from the group consisting of soluble or insoluble polyacrylamide, polyvinylimine, quadravalent ammonium, polyacrylate, carboxymethyl cellulose and alginate, based on 100% by volume of water.

6. The administration device according to claim 1, wherein said support (5) is mechanically attached or thermally bonded to the reservoir (2) and the needles (4) are thermally bonded to the support (5).

7. A separation-type transdermal administration kit of the patch-type which may be attached to the skin comprising the following:
   a) electrode (11) located uppermost and furthest from the place of skin attachment;
   b) solvent reservoir (12) for ionizing solvent and polyelectrolyte located below the electrode (11);
   c) semipermeable membrane (18) which may have a molecular weight cut off range in the range of from 200 to 20,000 which forms the lower portion of the solvent reservoir (12);
   d) drug reservoir (13) comprising a drug-immersed water swellable polymer located below the semipermeable membrane (18);
   e) patch body (30) comprising an adhesive layer (16) formed around the drug reservoir (13); and
   f) skin needles (14) fixed vertically in a skin needle plate (15) separated from the patch body.

8. A transdermal administration kit as claimed in claim 7, in which the semipermeable membrane (18) is selected from the group consisting of polypropylene, cellulose, and ethylene vinylacetate.

9. The kit according to claim 7 wherein the drug reservoir contains a drug selected from the group consisting of captopril, bradykinin, atriopeptin, calcitonin-gene factor, cholecystokinin (CCK-8, 32), β-endorphin, nerve growth factor, melanocyte inhibitor -I, gastrin antagonist, neuro-tension, somatotatin, interferon, cyclosporin, encephalins, albumin, insulin, vasopressins, oxytocin, growth hormone, LH (Leutinizing Hormone) and TRH (Thyrotropin Releasing Hormone).

10. The kit according to claim 7 wherein the ionizing solvent in the solvent reservoir contains 1 to 50% by volume of solvents selected from the group consisting of salt buffer solutions of phenol derivatives, acetic acid, hydrochloric acid, ammonia water, and caustic soda.

11. The kit according to claim 7 wherein the polyelectrolyte contained in the solvent reservoir contains 1 to 30% by volume of one or more polyelectrolytes selected from the group consisting of soluble or insoluble polyacrylamide, polyvinylimine, quadravalent ammonium, polyacrylate, carboxymethyl cellulose and alginate, based on 100% by volume of water.

12. The administration kit according to claim 7, wherein said needle plate and skin needles are attached to the drug reservoir and positioned opposite from the electrode.

13. The administration kit according to claim 7, wherein said needle plate comprises steeo or non-woven fabric and the needles (14) are thermally bonded to the support (5).

14. A transdermal administration method for a peptide drug comprising the steps of:
   i) contacting the drug immersed in polyelectrolyte with ionizing solvent composition wherein the drug is ionized,
   ii) forming the drug pathway on the skin epidermis by penetrating a plurality of skin needles into the skin epidermis at a treatment site
   iii) transferring the ionized drug into the skin at the treatment site by iontophoretic force.

15. The transdermal administration method according to claim 14, wherein the drug is selected from the group consisting of Captopril, bradykinin, atriopeptin, calcitonin gene factor, cholecystokinin (CCK-8, 32), β-endorphin, nerve growth factor, melanocyte inhibitor-I, gastrin antagonist, neuro-tension, somatotatin, interferon, cyclosporin, encephalins, albumin, insulin, vasopressins, oxytocin, growth hormone, LH(Leutinizing Hormone), TRH(Thyrotropin Releasing Hormone).

16. The transdermal administration method according to claim 14,
   wherein the ionizing solvent contains 1 to 50% by volume of solvents selected from the group consisting of salt buffer solutions of phenol derivatives, acetic acid, hydrochloric acid, ammonia water, and caustic soda; based on 100% by volume of water.

17. The transdermal administration method according to claim 14 wherein the polyelectrolyte is used for adjusting pH in drug solution and electrolytic medium, and contains 1 to 30% by volume of one or more polyelectrolytes selected from the group consisting of soluble or insoluble polyacrylamide, polyvinylimine, quadravalent ammonium, polyacrylate, carboxymethyl cellulose and alginate, based on 100% by volume of water.

18. A transdermal administration method for a drug selected from the group consisting of captopril, bradykinin, atriopeptin, calcitonin gene factor, cholecystokinin (CCK-8, 32), $\beta$-endorphin, nerve growth factor, melanocyte inhibitor -I, gastrin antagonist, neuro-tension, somatotatin, interferon, cyclosporin, encephalins, albumin, insulin, vasopressins, oxytocin, growth hormone, LH (Luetinizing Hormone) and TRH (Thyrotropin Releasing Hormone), comprising the steps of:

i) contacting the drug immersed in a polyelectrolyte with an ionizing solvent composition wherein, the ionizing solvent contains 1 to 50% by volume of solvents selected from the group consisting of salt buffer solutions of phenol derivatives, acetic acid, hydrochloric acid, ammonia water, and caustic soda; and the polyelectrolyte contains 1 to 30% by volume of one or more polyelectrolytes selected from the group consisting of soluble or insoluble polyacrylamide, polyvinylimine, quadravalent ammonium, polyacrylate, carboxymethyl cellulose and alginate, based on 100% by volume of water;

ii) forming the drug pathway on the skin by micropiercing by penetrating a plurality of skin needles into the skin epidermis at a treatment site; and iii) transferring the ionized drug into the skin at the treatment site by iontophoretic force.

19. The method according to claim 18 further comprising: abrading the skin in the area of administration prior to forming the drug pathway of step (ii).

* * * * *